US008257398B2

(12) United States Patent  (10) Patent No.: US 8,257,398 B2
Jackson  (45) Date of Patent: Sep. 4, 2012

(54) POLYAXIAL BONE SCREW WITH CAM CAPTURE

(76) Inventor: Roger P. Jackson, Prairie Village, KS (US)

( * ) Notice: Subject to any disclaimer, the term of this patent is extended or adjusted under 35 U.S.C. 154(b) by 1092 days.

(21) Appl. No.: 12/009,130

(22) Filed: Jan. 16, 2008

(65) Prior Publication Data

US 2008/0140136 A1 Jun. 12, 2008

Related U.S. Application Data

(63) Continuation-in-part of application No. 10/818,554, filed on Apr. 5, 2004, now Pat. No. 7,662,175, which is a continuation of application No. 10/464,633, filed on Jun. 18, 2003, now Pat. No. 6,716,214, and a continuation-in-part of application No. 10/651,003, filed on Aug. 28, 2003.

(60) Provisional application No. 60/881,641, filed on Jan. 22, 2007.

(51) Int. Cl.
 *A61B 17/70* (2006.01)
(52) U.S. Cl. ........................................................ 606/264
(58) Field of Classification Search .................. 606/246, 606/264–268, 270, 272, 278, 279, 301, 305, 606/306, 308, 328
See application file for complete search history.

(56) References Cited

U.S. PATENT DOCUMENTS

| 2,346,346 | A | 4/1944 | Anderson |
|---|---|---|---|
| 2,362,999 | A | 11/1944 | Elmer |
| 2,531,892 | A | 11/1950 | Reese |
| 2,813,450 | A | 11/1957 | Dzus |
| 3,013,244 | A | 12/1961 | Rudy |
| 4,033,139 | A | 7/1977 | Frederick |
| 4,759,672 | A | 7/1988 | Nilsen et al. |
| 4,790,297 | A | 12/1988 | Luque |
| 4,946,458 | A | 8/1990 | Harms et al. |
| 5,019,080 | A | 5/1991 | Hemer |
| 5,056,492 | A | 10/1991 | Banse |
| 5,129,388 | A | 7/1992 | Vignaud et al. |
| 5,207,678 | A | 5/1993 | Harms et al. |
| 5,261,912 | A | 11/1993 | Frigg |
| 5,312,404 | A | 5/1994 | Asher et al. |
| 5,360,431 | A | 11/1994 | Puno et al. |
| 5,395,371 | A | 3/1995 | Miller et al. |
| 5,429,639 | A | 7/1995 | Judet |
| 5,443,467 | A | 8/1995 | Biedermann et al. |
| 5,466,237 | A | 11/1995 | Byrd, III et al. |

(Continued)

FOREIGN PATENT DOCUMENTS

DE 19507141 9/1996

(Continued)

OTHER PUBLICATIONS

*EBI Omega 21* Brochure, EBI Spine Systems, pub. 1999.

(Continued)

*Primary Examiner* — Eduardo C Robert
*Assistant Examiner* — David Comstock
(74) *Attorney, Agent, or Firm* — John C. McMahon

(57) ABSTRACT

A polyaxial bone screw assembly includes a threaded shank body having an upper portion with a laterally extending lug and a retainer having an inner cam track for receiving the lug and thus attaching the shank upper portion to the retainer within a receiver. The retainer may be a closed or open ring. The receiver has a cavity and a U-shaped cradle defining a channel for receiving a longitudinal connecting member such as a spinal fixation rod. The retainer has an external surface that mates with an internal surface of the receiver, providing a ball joint.

24 Claims, 6 Drawing Sheets

U.S. PATENT DOCUMENTS

| | | | |
|---|---|---|---|
| 5,474,555 A | 12/1995 | Puno et al. |
| 5,476,462 A | 12/1995 | Allard et al. |
| 5,476,464 A | 12/1995 | Metz-Stavenhagen et al. |
| 5,496,321 A | 3/1996 | Puno et al. |
| 5,554,157 A | 9/1996 | Errico et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,426 A | 3/1997 | Ralph et al. |
| 5,647,873 A | 7/1997 | Errico et al. |
| 5,669,911 A | 9/1997 | Errico et al. |
| 5,672,176 A | 9/1997 | Biedermann et al. |
| 5,681,319 A | 10/1997 | Biedermann et al. |
| 5,690,630 A | 11/1997 | Errico et al. |
| 5,716,356 A | 2/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,797,911 A | 8/1998 | Sherman et al. |
| 5,800,435 A | 9/1998 | Errico et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| 5,938,663 A | 8/1999 | Petreto |
| 5,954,725 A | 9/1999 | Sherman et al. |
| 5,961,517 A | 10/1999 | Biedermann et al. |
| 5,964,760 A | 10/1999 | Richelsoph |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,132,431 A | 10/2000 | Nilsson et al. |
| 6,132,432 A | 10/2000 | Richelsoph |
| 6,132,434 A | 10/2000 | Sherman et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,214,012 B1 | 4/2001 | Karpman et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger et al. |
| 6,309,391 B1 | 10/2001 | Crandall et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,402,752 B2 | 6/2002 | Schaffler-Wachter et al. |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,547,790 B2 | 4/2003 | Harkey, III et al. |
| 6,551,320 B2 | 4/2003 | Lieberman |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,652,526 B1 | 11/2003 | Arafiles |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,677 B1 | 5/2005 | Lin |
| 6,932,817 B2 | 8/2005 | Baynham et al. |
| 6,945,972 B2 | 9/2005 | Frigg et al. |

| | | |
|---|---|---|
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| RE39,089 E | 5/2006 | Ralph et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,125,426 B2 | 10/2006 | Moumene et al. |
| 7,128,743 B2 | 10/2006 | Metz-Stavenhagen |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,186,255 B2 | 3/2007 | Baynham et al. |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,264,621 B2 | 9/2007 | Coates et al. |
| 7,270,665 B2 | 9/2007 | Morrison et al. |
| 7,291,151 B2 | 11/2007 | Alvarez |
| 7,291,153 B2 | 11/2007 | Glascott |
| 7,294,128 B2 | 11/2007 | Alleyne et al. |
| 7,294,129 B2 | 11/2007 | Hawkins et al. |
| 2001/0001119 A1 | 5/2001 | Lombardo |
| 2002/0035366 A1 | 3/2002 | Walder et al. |
| 2002/0045898 A1 | 4/2002 | Freid et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133159 A1 | 9/2002 | Jackson |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131413 A1 | 6/2005 | O'Driscoll et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203516 A1 | 9/2005 | Biedermann et al. |
| 2005/0216003 A1 | 9/2005 | Biedermann et al. |
| 2005/0228379 A1 | 10/2005 | Jackson |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0260058 A1 | 11/2005 | Cassagne, III |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Lieberman |
| 2006/0009770 A1 | 1/2006 | Speirs et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079899 A1 | 4/2006 | Ritland |
| 2006/0084981 A1 | 4/2006 | Shluzas |
| 2006/0084989 A1 | 4/2006 | Dickinson et al. |
| 2006/0084993 A1 | 4/2006 | Landry et al. |
| 2006/0084995 A1 | 4/2006 | Biedermann et al. |
| 2006/0089643 A1 | 4/2006 | Mujwid |
| 2006/0089644 A1 | 4/2006 | Felix |
| 2006/0095037 A1 | 5/2006 | Jones et al. |
| 2006/0100621 A1 | 5/2006 | Jackson |
| 2006/0106380 A1 | 5/2006 | Colleran et al. |
| 2006/0106383 A1 | 5/2006 | Biedermann et al. |
| 2006/0116677 A1 | 6/2006 | Burd et al. |
| 2006/0129147 A1 | 6/2006 | Biedermann et al. |
| 2006/0129149 A1 | 6/2006 | Iott et al. |
| 2006/0142761 A1 | 6/2006 | Landry et al. |
| 2006/0149232 A1 | 7/2006 | Sasing |
| 2006/0149241 A1 | 7/2006 | Richelsoph et al. |

| | | |
|---|---|---|
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0195098 A1 | 8/2006 | Schumacher |
| 2006/0200123 A1 | 9/2006 | Ryan |
| 2006/0200131 A1 | 9/2006 | Chao et al. |
| 2006/0200149 A1 | 9/2006 | Hoy et al. |
| 2006/0212034 A1 | 9/2006 | Triplett et al. |
| 2006/0217716 A1 | 9/2006 | Baker et al. |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0247624 A1 | 11/2006 | Banouskou et al. |
| 2006/0247631 A1 | 11/2006 | Ahn et al. |
| 2006/0247636 A1 | 11/2006 | Yuan et al. |
| 2006/0247779 A1 | 11/2006 | Gordon et al. |
| 2006/0264933 A1 | 11/2006 | Baker et al. |
| 2006/0264936 A1 | 11/2006 | Partin et al. |
| 2006/0276787 A1 | 12/2006 | Zubok et al. |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0293659 A1 | 12/2006 | Alvarez |
| 2006/0293665 A1 | 12/2006 | Shluzas |
| 2006/0293666 A1 | 12/2006 | Matthis et al. |
| 2007/0016188 A1 | 1/2007 | Boehm, Jr. et al. |
| 2007/0016198 A1 | 1/2007 | Boehm, Jr. et al. |
| 2007/0021750 A1 | 1/2007 | Shluzas et al. |
| 2007/0043355 A1 | 2/2007 | Bette et al. |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049933 A1 | 3/2007 | Ahn et al. |
| 2007/0055235 A1 | 3/2007 | Janowski et al. |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0073291 A1 | 3/2007 | Cordaro et al. |
| 2007/0078460 A1 | 4/2007 | Frigg et al. |
| 2007/0083199 A1 | 4/2007 | Baccelli |
| 2007/0088357 A1 | 4/2007 | Johnson et al. |
| 2007/0093817 A1 | 4/2007 | Barrus et al. |
| 2007/0093818 A1 | 4/2007 | Biedermann et al. |
| 2007/0093823 A1 | 4/2007 | Albert |
| 2007/0093826 A1 | 4/2007 | Hawkes et al. |
| 2007/0093827 A1 | 4/2007 | Warnick |
| 2007/0093831 A1 | 4/2007 | Abdelgany et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123867 A1 | 5/2007 | Kirschman |
| 2007/0123870 A1 | 5/2007 | Jeon et al. |
| 2007/0161986 A1 | 7/2007 | Levy |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173819 A1 | 7/2007 | Sandlin |
| 2007/0173820 A1 | 7/2007 | Trieu |
| 2007/0173828 A1 | 7/2007 | Firkins et al. |
| 2007/0191839 A1 | 8/2007 | Justis et al. |
| 2007/0198014 A1 | 8/2007 | Graf et al. |
| 2007/0208344 A1 | 9/2007 | Young |
| 2007/0225707 A1 | 9/2007 | Wisnewski et al. |
| 2007/0225711 A1 | 9/2007 | Ensign |
| 2007/0233078 A1 | 10/2007 | Justis et al. |
| 2007/0233080 A1 | 10/2007 | Na et al. |
| 2007/0233086 A1 | 10/2007 | Harms et al. |
| 2007/0233087 A1 | 10/2007 | Schlapfer |
| 2007/0250061 A1 | 10/2007 | Chin et al. |
| 2007/0260243 A1 | 11/2007 | Kagami |

FOREIGN PATENT DOCUMENTS

| | | |
|---|---|---|
| EP | 1121902 | 8/2001 |
| EP | 1190678 | 3/2002 |
| EP | 1570795 | 9/2005 |
| EP | 1579816 | 9/2005 |
| EP | 1634537 | 3/2006 |
| FR | 2729291 | 7/1996 |
| FR | 2796545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 9202745.8 | 4/1992 |
| GB | 2365345 | 2/2002 |
| WO | WO01/49191 | 7/2001 |
| WO | WO02/054966 | 7/2002 |
| WO | WO03/068088 | 8/2003 |
| WO | WO2004/041100 | 5/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO2005/099400 | 10/2005 |
| WO | WO2006/005198 | 1/2006 |
| WO | WO2006/012088 | 2/2006 |
| WO | WO2006/017616 | 2/2006 |
| WO | WO2006/028537 | 3/2006 |
| WO | WO2006/119241 | 11/2006 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |

OTHER PUBLICATIONS

*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*SDRS Surgical Dynamics Rod System* Brochure, Surgical Dynamics, pub. 1998-99.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.

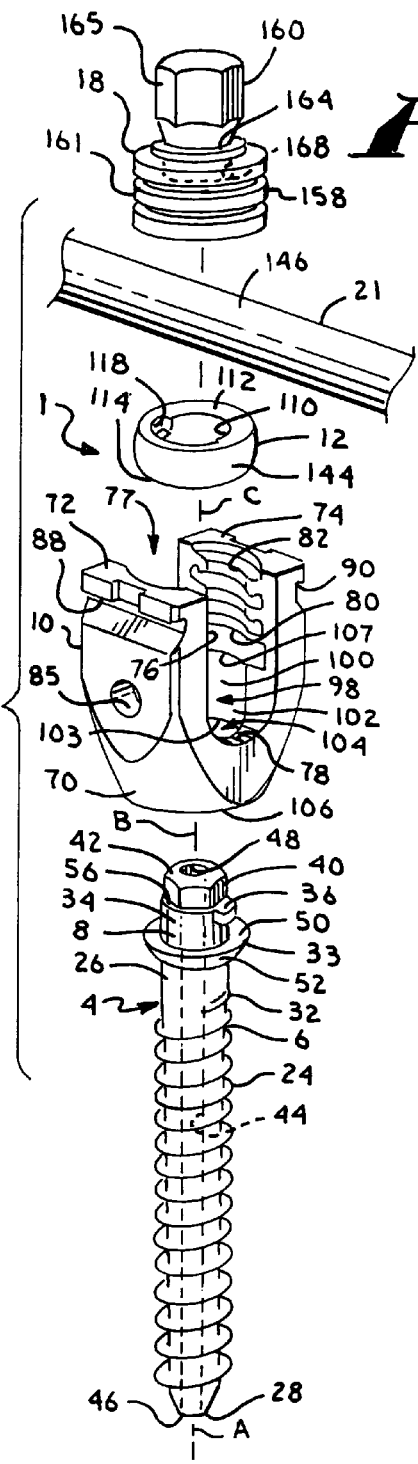
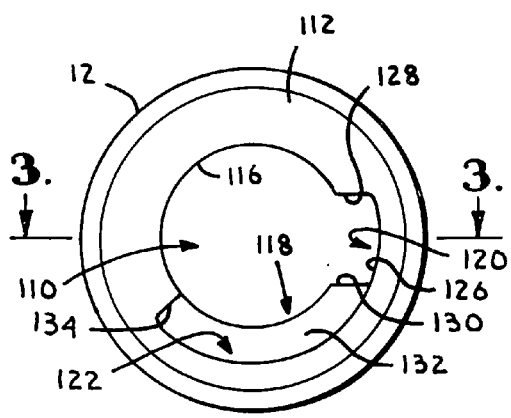
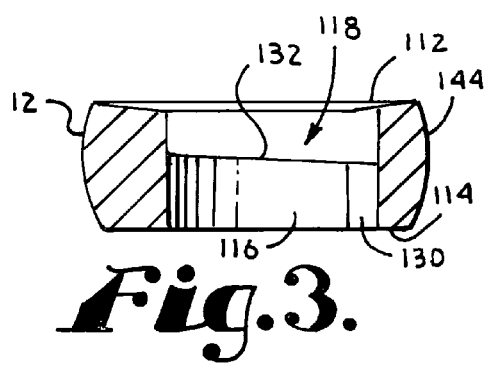

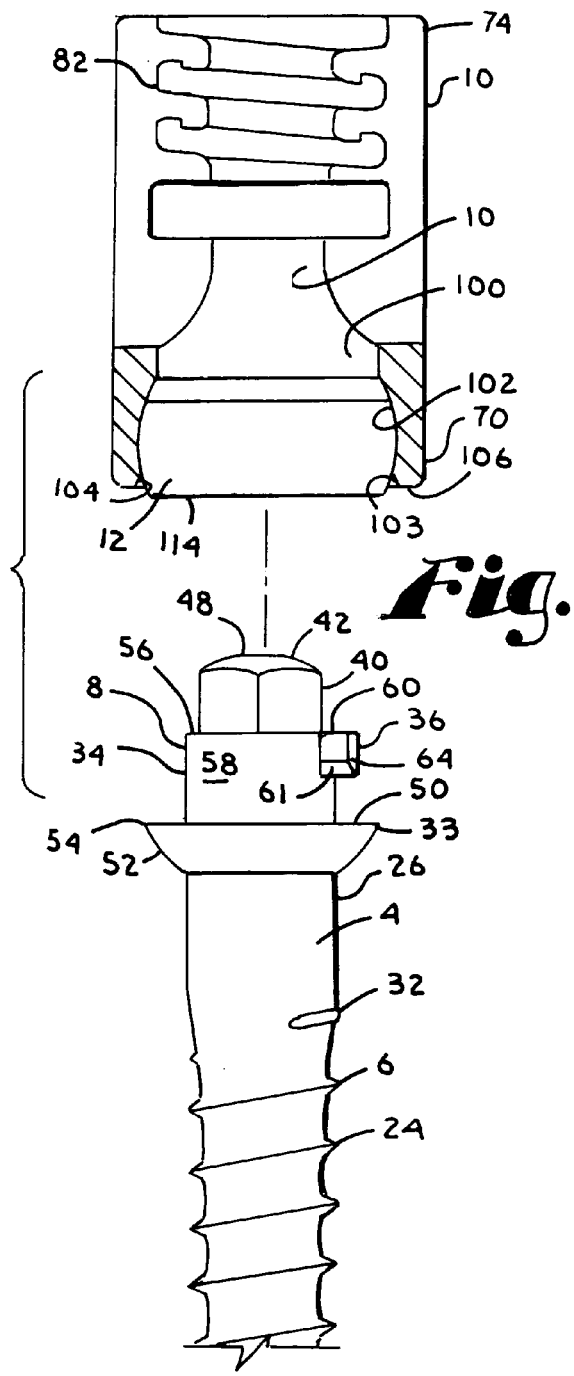
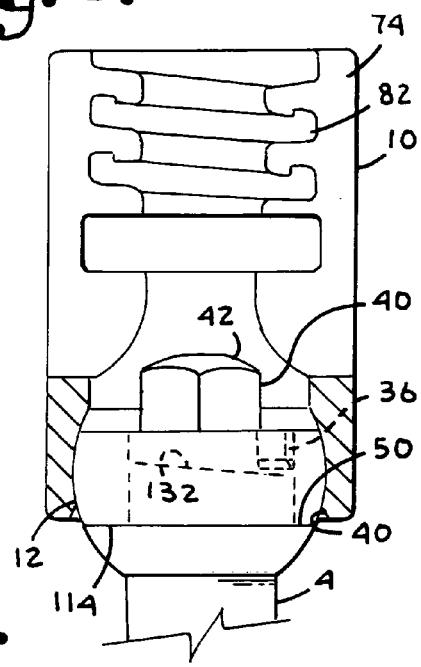
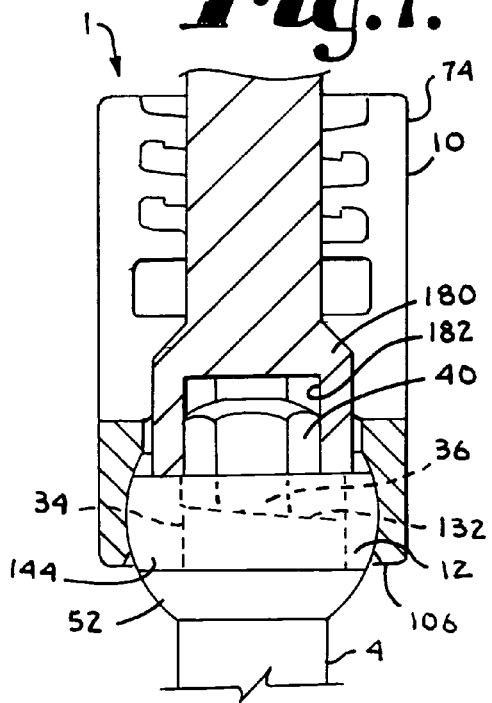

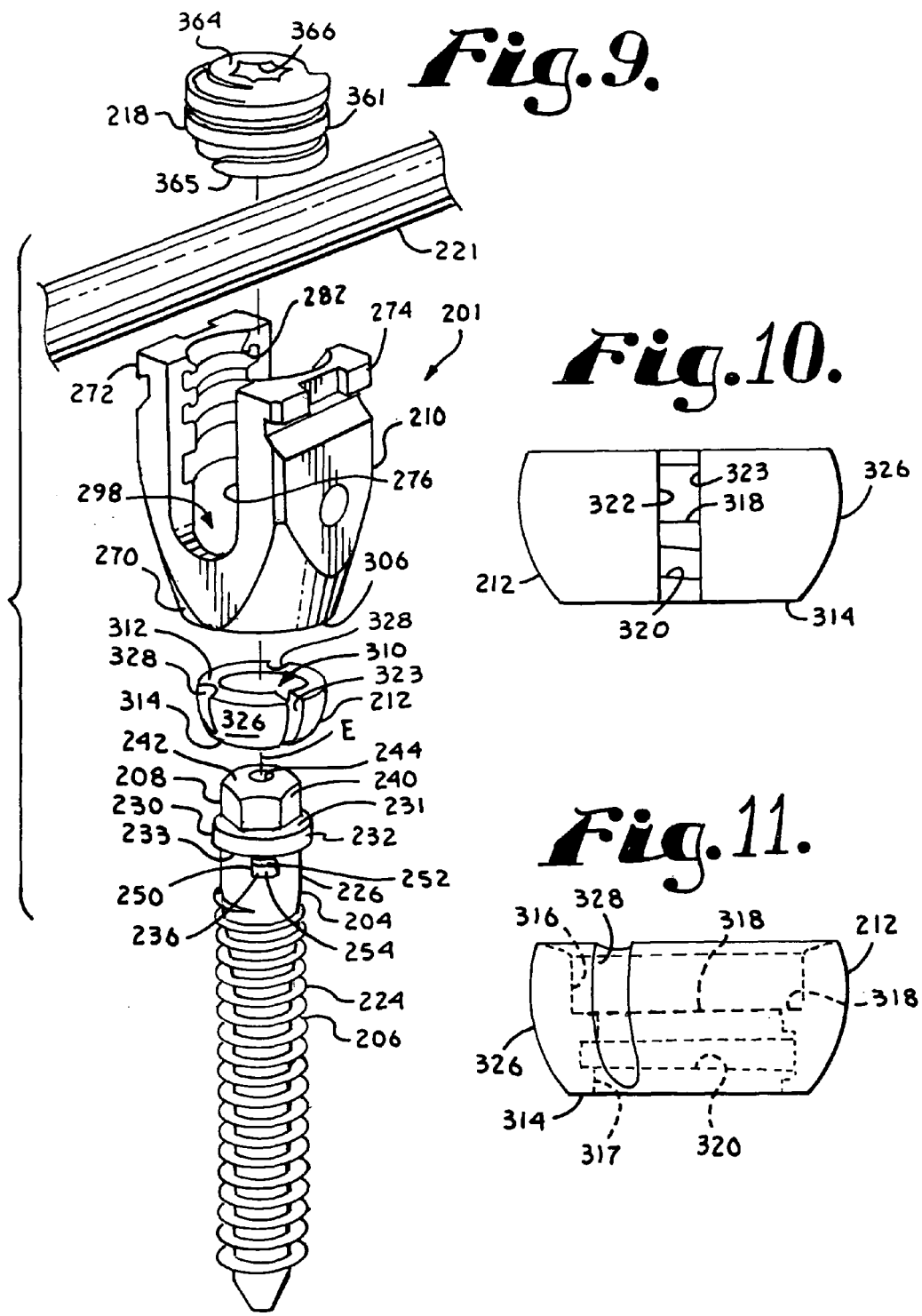

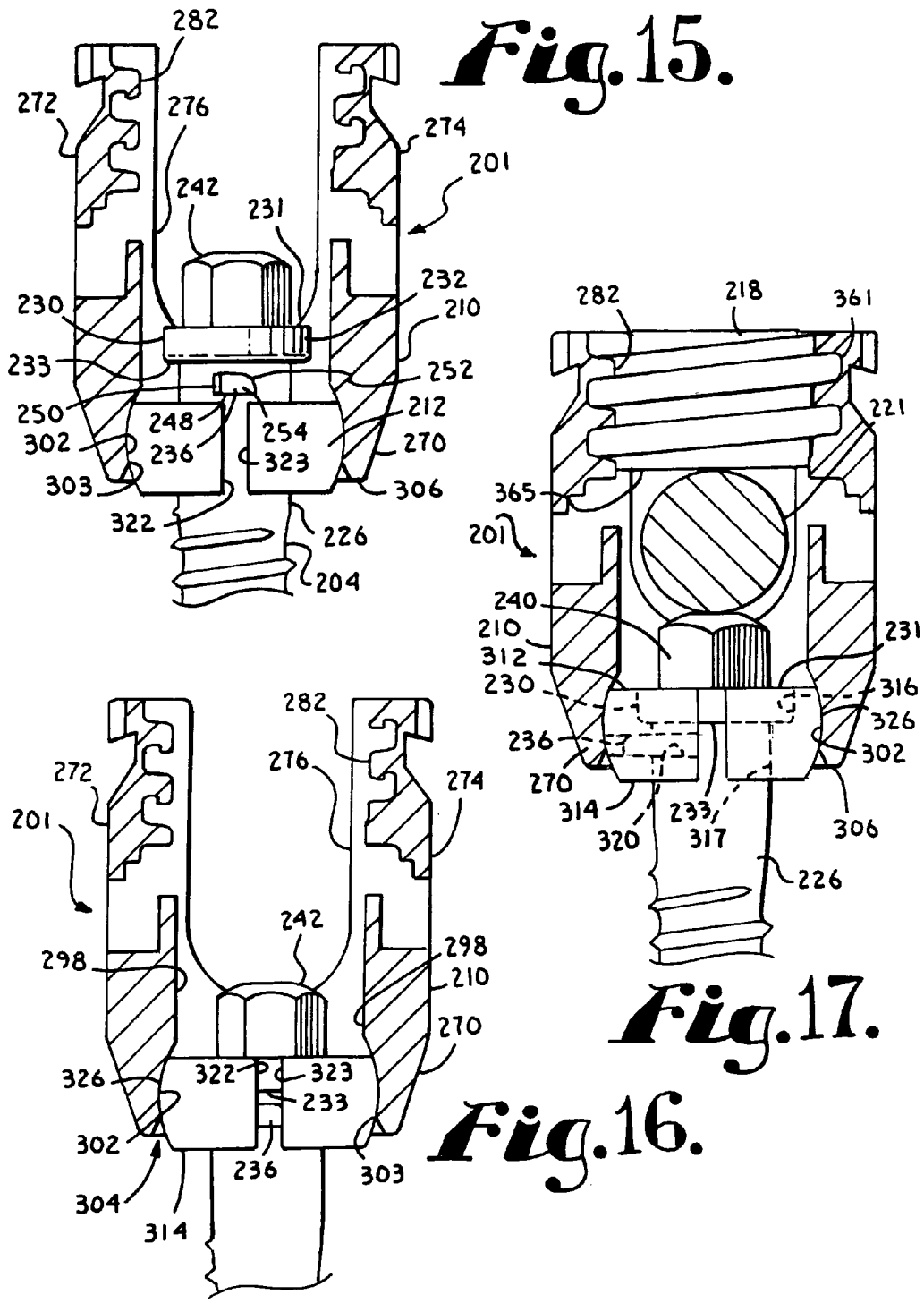

POLYAXIAL BONE SCREW WITH CAM CAPTURE

CROSS REFERENCE TO RELATED APPLICATIONS

This application claims the benefit of U.S. Provisional Application No. 60/881,641 filed Jan. 22, 2007 and incorporated by reference herein. This application is also a continuation-in-part of U.S. patent application Ser. No. 10/818,554, filed Apr. 5, 2004 which is a continuation of U.S. patent application Ser. No. 10/464,633, filed Jun. 18, 2003, now U.S. Pat. No. 6,716,214. U.S. patent application Ser. No. 10/818,554 is also a continuation-in-part of U.S. patent application Ser. No. 10/651,003, filed Aug. 28, 2003.

BACKGROUND OF THE INVENTION

The present invention is directed to polyaxial bone screws for use in bone surgery, particularly spinal surgery. Such screws have a receiver or head that can swivel about a shank of the bone screw, allowing the receiver to be positioned in any of a number of angular configurations relative to the shank.

Many spinal surgery procedures require securing various implants to bone and especially to vertebrae along the spine. For example, elongate members, such as solid rigid rods or more flexible elongate members are often utilized that extend along the spine to provide support to vertebrae that have been damaged or weakened due to injury or disease. Such elongate members must be supported by certain vertebrae and support other vertebrae.

The most common mechanism for providing vertebral support is to implant bone screws into certain bones which then in turn support the elongate member or are supported by the elongate member. Bone screws of this type may have a fixed head or receiver relative to a shank thereof. In the fixed bone screws, the head cannot be moved relative to the shank and the rod must be favorably positioned in order for it to be placed within the head. This is sometimes very difficult or impossible to do. Therefore, polyaxial bone screws are commonly preferred.

Polyaxial bone screws allow rotation of the receiver about the shank until a desired rotational position of the receiver is achieved relative to the shank. Thereafter, a rod can be inserted into the receiver and eventually the receiver is locked or fixed in a particular position relative to the shank.

A variety of polyaxial or swivel-head bone screw assemblies are available. One type of bone screw assembly includes an open head or receiver that allows for placement of a rod within the receiver. A closure top or plug is then used to capture the rod in the receiver of the screw.

SUMMARY OF THE INVENTION

A polyaxial bone screw assembly of the present invention includes a shank having a generally elongate body with an upper end portion and a lower threaded portion for fixation to a bone. The upper end portion further includes a laterally extending lug. The shank is up loadable into a receiver. The receiver has a top portion and a base, the top portion being open and having a channel. The base includes an inner seating surface partially defining a cavity and a lower aperture or opening. The channel of the top portion communicates with the cavity. The lower opening is sized and shaped to receive the shank upper portion into the receiver cavity.

The bone screw assembly also includes a retainer structure that in some embodiments is a contiguously closed ring-like retainer and in other embodiments is an open or discontinuous ring. The retainer has an inner ramped slot or cam track with at least one surface frictionally engaging the laterally extending lug, thereby securing the retainer to the shank.

OBJECTS AND ADVANTAGES OF THE INVENTION

Therefore, objects of the invention include: providing an implant wherein all of the parts remain together and do not separate; providing a lightweight, low profile polyaxial bone screw that assembles in such a manner that the components cooperate to create an overall structure that prevents unintentional disassembly; providing a polyaxial bone screw with features that provide adequate frictional or gripping surfaces for bone implantation tools and may be readily, securely fastened to each other and to bone; and providing apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a an exploded perspective view of a polyaxial bone screw assembly according to the present invention having a shank, a receiver, and a retainer with cam track and further shown with a rod and a closure structure.

FIG. 2 is an enlarged top plan view of the retainer of FIG. 1.

FIG. 3 is an enlarged cross-sectional view taken along the line 3-3 of FIG. 2.

FIG. 5 is a partial exploded view of the shank, retainer and receiver of FIG. 1 with portions broken away to show the detail thereof.

FIG. 6 is a partial view similar to FIG. 5 showing the shank being uploaded into the retainer in a stage of assembly therewith cam connection shown in phantom.

FIG. 7 is a partial view similar to FIGS. 5 and 6 showing the shank after rotation into a frictionally engaged locked assembled position with respect to the retainer with cam connection shown in phantom and further shown with a holding tool.

FIG. 9 is a an exploded perspective view of a second embodiment of a polyaxial bone screw assembly according to the present invention having a shank, a receiver, and a retainer with cam track and further shown with a rod and a closure structure.

FIG. 10 is an enlarged front elevational view of the retainer of FIG. 9.

FIG. 11 is an enlarged rear elevational view of the retainer of FIG. 9 and showing the cam track in phantom.

FIG. 15 is a partial front elevation view of the shank, retainer and receiver of FIG. 9 showing the shank and connected retainer of FIG. 14 loaded into the retainer in a stage of assembly therewith portions broken away to show detail of the receiver.

FIG. 16 is a partial view similar to FIG. 15 showing the shank prior to rotation into a frictionally engaged locked assembled position with the retainer.

FIG. 17 is a partial view similar to FIG. 16 showing the shank after rotation into a frictionally engaged locked assembled position with respect to the retainer with cam connection shown in phantom and further shown the closure of FIG. 9.

DETAILED DESCRIPTION OF THE INVENTION

Figure 8:
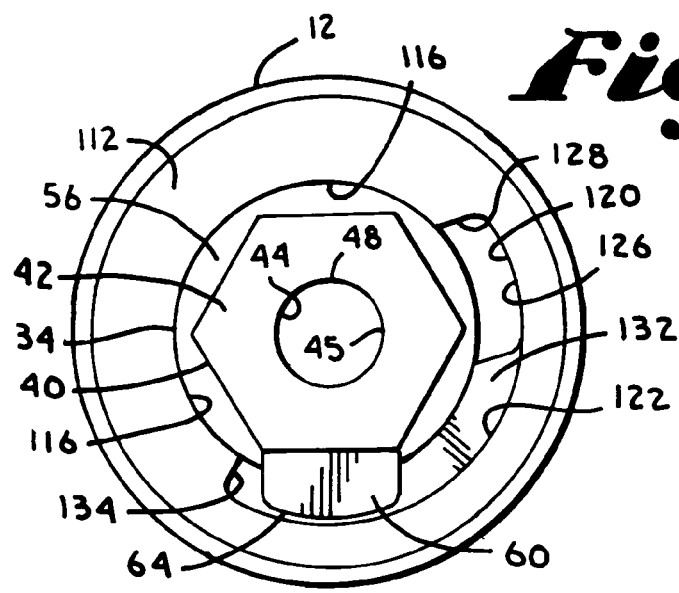
FIG. 8 is an enlarged top plan view of the shank and retainer of FIG. 1 shown in the locked orientation of FIG. 7.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of bone attachment assemblies of the application and cooperating connecting members in actual use.

With reference to FIGS. 1-8, the reference number 1 generally represents an embodiment of a polyaxial bone screw apparatus or assembly according to the present invention. The assembly 1 includes a shank 4 that further includes a threaded body 6 integral with an upper portion 8; a receiver 10; and a closed or integral retainer structure 12 or ring 12. The shank 4, receiver 10 and retainer structure 12 preferably are factory assembled prior to implantation of the shank body 6 into a vertebra (not shown).

With further reference to FIG. 1, also shown is a closure structure 18 for biasing a longitudinal connecting member such as a rod 21 against the shank upper portion 8 which biases the retainer 12 into fixed frictional contact with the receiver 10, so as to fix the rod 21 relative to the vertebra (not shown). The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

The shank 4, best illustrated in FIGS. 1, 4, 5 and 8, is elongate, with the shank body 6 having a helically wound bone implantable thread 24 extending from near a neck 26 located adjacent to the upper portion 8 to a tip 28 of the body 6 and extending radially outwardly therefrom. During use, the body 6 utilizing the thread 24 for gripping and advancement is implanted into the vertebra (not shown) leading with the tip 28 and driven down into the vertebra with an installation or driving tool, so as to be implanted in the vertebra to near the neck 26, and as is described more fully in the paragraphs below. The shank 4 has an elongate axis of rotation generally identified by the reference letter A.

The neck 26 extends axially upwardly from the shank body 6. The neck 26 may be of reduced radius as compared to an adjacent top 32 of the threaded body 6. Further extending axially upwardly from the neck 26 is the shank upper portion 8 that provides a connective or capture apparatus disposed at a distance from the threaded body top 32 and thus at a distance from the vertebra when the body 6 is implanted in the vertebra.

The shank upper portion 8 is configured for a polyaxial connection between the shank 4 and the receiver 10 and capturing the shank 4 upper portion 8 in the receiver 10. The upper portion 8 generally includes a retainer seat portion 33; a substantially cylindrical portion 34 having a laterally extending extension in the form of a lug or tab 36; a tool engagement structure 40 and a top end surface 42. A driving tool (not shown) is configured to fit about the tool engagement structure 40 so as to form a socket and mating projection for both driving and rotating the shank body 6 into the vertebra. In the embodiment shown in the figures, the tool engagement structure 40 is in the shape of a hexagonally shaped extension head coaxial with both the threaded shank body 6 and the shank upper portion 8. Other embodiments of the invention may include up to a plurality of lugs 36, for example, a pair of opposed lateral lugs.

The top end surface 42 of the shank 4 is preferably curved or dome-shaped as shown in the drawings, for contact engagement or positive mating engagement with the rod 21, when the bone screw assembly 1 is assembled, as shown in FIG. 7 and in any alignment of the shank 4 relative to the receiver 10. In certain embodiments, the surface 42 is smooth. While not required in accordance with practice of the invention, the surface 42 may be scored or knurled to further increase frictional positive mating engagement between the surface 42 and the rod 21.

The shank 4 shown in the drawings is cannulated, having a small central bore 44 extending an entire length of the shank 4 along the axis A. The bore 44 is defined by an inner cylindrical wall 45 of the shank 4 and has a first circular opening 46 at the shank tip 28 and a second circular opening 48 at the top surface 42. The bore 44 is coaxial with the threaded body 6 and the capture structure outer surface 34. The bore 44 provides a passage through the shank 4 interior for a length of wire (not shown) inserted into the vertebra (not shown) prior to the insertion of the shank body 6, the wire providing a guide for insertion of the shank body 6 into the vertebra.

Figure 4:
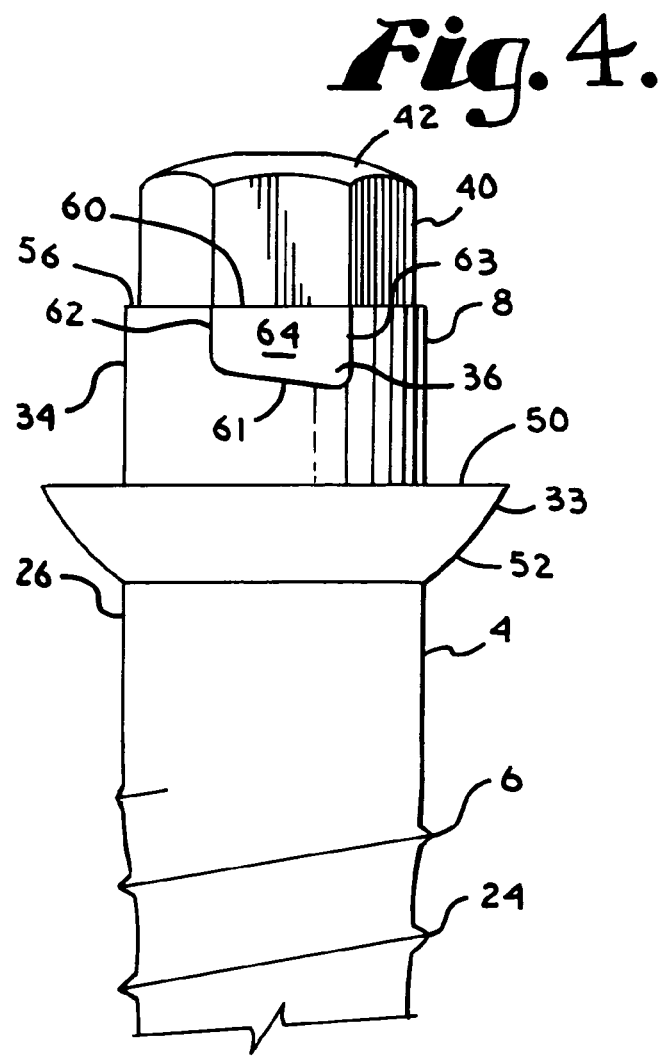
FIG. 4 is an enlarged front elevational view of the shank of FIG. 1.

With reference to FIGS. 4 and 5, the retainer seat 33 of the shank upper portion 8 includes a substantially planar annular upper surface 50 disposed perpendicular to the Axis A of the shank and sized and shaped to be bottom loaded in the receiver 10 with a radially extending width sufficient for frictional mating with the retainer 12 as will be described in greater detail subsequently herein. The seat 33 further includes a substantially spherically shaped surface 52 extending from an edge or rim 54 of the flat annular surface 50 and curving downwardly toward the shank body 6 to the neck 26. Although a spherical surface 52 is shown, it is noted that the surface may be conical or otherwise non-spherically curved. In the disclosed embodiment, the surface 52 is flush with an outer surface of the retainer 12 when the seat 33 engages the retainer 12 as will be discussed below.

The cylindrical portion 34 of the shank upper portion 8 is disposed between the seat portion 33 and the tool engagement structure 40. The portion 34 includes a top surface or narrow ledge 56 and a substantially smooth cylindrical surface 58 that runs from the ledge 56 to the annular surface 50 of the seat 33. The surface 58 is uniform about the axis A. The lug 36 extends laterally from the surface 58 near the ledge 56. The lug 36 includes a top surface 60, a bottom surface 61, a pair of opposed and substantially parallel side surfaces 62 and 63 and an outer curved surface 64. The curved surface 64 is cylindrical and coaxial with the surface 58. The top surface 60 extends from the tool engagement structure 40 and in some embodiments may slope slightly downwardly toward the seat 33 as well as outwardly toward the outer surface 64 as illustrated. The bottom surface 61 extends from the cylindrical surface 58 to the outer surface 64. As best illustrated in FIG. 4, the bottom surface 61 is also preferably sloped or ramped at an angle directed downwardly from the side 62 to the side 63 so as to fully frictionally engage a cam track ramped surface of the retainer 12 as will be described in greater detail below. It is foreseen that the bottom surface 61 may also be disposed generally parallel to the seating surface 50 resulting in an edge of the bottom surface 61 ultimately in frictional locking engagement with the cam track of the retainer 12.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

Referring to FIGS. 1 and 5, the receiver 10 has a generally U-shaped appearance with a partially cylindrical inner profile and a partially curved and partially faceted outer profile; however, the outer profile could also be partially cylindrical. The receiver 10 includes a somewhat curved or spherical base 70 integral with a pair of upstanding arms 72 and 74 forming a U-shaped cradle and defining a U-shaped channel 76 between the arms 72 and 74 with an upper opening 77 and a lower seat 78 having substantially the same radius as the rod 21 for operably snugly receiving the rod 21.

Each of the arms 72 and 74 has an interior surface 80 that defines the inner cylindrical profile and includes a partial helically wound guide and advancement structure 82. In the illustrated embodiment, the guide and advancement structure 82 is a partial helically wound interlocking square thread configured to mate under rotation with a similar structure on the closure structure 18, as described more fully below. However, it is foreseen that the guide and advancement structure 82 could alternatively be a flange form, a buttress thread, a reverse angle thread or other thread like or non-thread like helically wound advancement structures for operably guiding under rotation and advancing the closure top downward between the arms 72 and 74.

Tool engaging apertures 85 are formed on or through surfaces of the arms 72 and 74 that may be used for holding the receiver 10 during assembly with the shank 4 and the retainer structure 12 and also during the implantation of the shank body 6 into a vertebra (not shown). Furthermore, each of the arms 72 and 74 also includes a V-shaped or undercut tool engagement groove 88 and 90, respectively, formed on outer surfaces thereof which may be used for holding the receiver 10 with a holding tool (not shown) having projections that are received within the grooves 88 and 90 during implantation of the shank body 6 and/or during subsequent installation of the rod 21 and the closure structure 18. It is foreseen that tool receiving grooves or apertures may be configured in a variety of shapes and sizes and be disposed at other locations on the receiver arms 72 and 74.

Communicating with and located beneath the U-shaped channel 76 of the receiver 10 is a chamber or cavity 98 substantially defined by an inner surface 100 of the base 70, the cavity 98 opens upwardly into the U-shaped channel 76. The inner surface 100 is substantially spherical, with at least a portion thereof forming a partial internal spherical seating surface 102 having a first radius. The surface 102 is sized and shaped for mating with the retainer structure 12, as described more fully below.

The base 70 further includes a restrictive neck 103, having a second radius R and defining a bore 104 communicating with the cavity 98 and a lower exterior 106 of the base 50. The bore 104 is coaxially aligned with respect to a rotational axis B of the receiver 10. The neck 103 and associated bore 104 are sized and shaped to be smaller (the second radius) than a radial dimension of the retainer structure 12 (the first radius), so as to form a restriction at the location of the neck 103 relative to the retainer structure 12, to prevent the retainer structure 12 from passing from the cavity 98 and out into the lower exterior 106 of the receiver 10 when the retainer structure 12 is seated within the receiver 10.

The inner surface 100 further defines an elongate upper loading recess 107 for accommodating and loading the retainer structure 12 into the cavity 98. The loading recess 107 is generally vertically disposed in the receiver 10, extending between and communicating with both the channel 76 and the cavity 98, allowing for ease in top loading the retainer structure 12 into the cavity through the upper opening 77 and otherwise allowing for the spherical wall 100 of the receiver 10 to have a comparatively enlarged radius to allow for increased thickness and strength of the receiver base 70; however, the loading recess 107 is not always necessary.

The retainer structure or ring 12 is used to capture the shank upper portion 8 and retain the upper portion 8 within the receiver 10. The retainer 12, best illustrated in FIGS. 2, 3 and 8, has an operational central axis that is the same as the rotational axis A associated with the shank 4, but when the retainer structure 12 is separated from the shank 4, the axis of rotation is identified as axis C, as shown in FIG. 1. The retainer structure 12 has a central bore 110 that passes entirely through the retainer structure 12 from a top surface 112 to a bottom surface 114 thereof. The bottom surface 114 is substantially planar and disposed perpendicular to the axis C. A first inner cylindrical surface 116 defines a substantial portion of the bore 110. The cylindrical surface 116 is sized and shaped to be slidingly received about the cylindrical surface portion 34 of the shank upper portion 8. A slot, generally 118 is formed in the inner surface 116 and also portions of the top surface 112 and the bottom surface 114. The slot 118 may be further described as including a through slot, generally 120 and a cam track, generally 122, the through slot 120 cooperating and communicating with the cam track 122. The through slot 120 is sized and shaped to receive the lug 36 of the shank upper portion therethrough during installation of the retainer 12 on the shank upper portion 8 within the receiver cavity 98. The cam track 122 is sized and shaped to frictionally engage the bottom surface 61 of the lug 36 of the shank upper portion 8, with the retainer 12 bottom surface 114 being seated on the upper surface 50 of the seat 33 of the shank upper portion 8.

With particular reference to FIGS. 2 and 3, the through slot 120 is defined by an inner cylindrical surface 126 coaxial with the cylindrical surface 116. The cylindrical surface 126 also partially defines the cam track 122. At the slot 120, the surface 126 extends between and through the top surface 112 and the bottom surface 114. The through slot 120 is further defined by opposed side surfaces 128 and 130, both of which run parallel to the axis C. The side surface 128 extends between and through the top surface 112 and the bottom surface 114. The side surface 130 begins at the bottom surface 114 and ends at a ramped surface 132 that partially defines the cam track 122. The cam track 122 is further defined by the inner cylindrical surface 126 that extends to a surface or stop 134 that runs substantially parallel to the axis C. Thus, the cam track 122 is defined by a portion of the cylindrical surface 126, the ramped or sloped surface 132 and the stop 134. The ramped surface 132 slopes upwardly in a direction toward the top surface 112 as the surface 132 runs from the surface 130 to the stop 134. A degree of inclination of the surface 132 substantially matches a degree of inclination of the bottom surface 61 of the lug 36. In some embodiments according to the invention, one or both the ramped surface 132 and the lug bottom surface 61 includes a roughening, ridges or some other treatment to further aid frictional locking of the retainer 12 with respect to the lug 36.

The top surface 112 of the retainer 12 in cooperation with the ledge 56 of the shank upper portion 8 provide a surface about the tool engagement structure 40 that is a stable seating surface for the driving tool (not shown). The illustrated slightly curved top surface 112 provides somewhat of a recess to better grip the driving tool. It is also foreseen that the top surface 112 may be planar or include recesses or apertures for receiving a holding tool therein.

The retainer 12 also has a radially outer partially spherically shaped surface 144 sized and shaped to mate with the partial spherical shaped seating surface 102 of the receiver and having a third radius approximately equal to the first radius associated with the surface 102. The retainer structure third radius is larger than the second radius of the neck 103 of the receiver 10. Although not required, it is foreseen that the outer partially spherically shaped surface 144 may be a high friction surface such as a knurled surface or the like.

The elongate rod or longitudinal member 21 that is utilized with the assembly 1 can be any of a variety of implants utilized in reconstructive spinal surgery, but is normally a cylindrical elongate structure having a cylindrical surface 146 of uniform diameter and having a generally smooth surface. The longitudinal connecting member 21 may be made from metal, metal alloys or other suitable materials, including plastic polymers such as polyetheretherketone (PEEK), ultra-high-molecular weight-polyethylene (UHMWP), polyurethanes and composites. The illustrated rod 21 is preferably sized and shaped to snugly seat near the bottom of the U-shaped channel 76 of the receiver 10 and, during normal operation, is positioned slightly above the bottom of the channel 76 at the lower seat 78. In particular, the rod 21 normally directly or abutingly engages the shank top surface 42 and is biased against the dome shank top surface 42, consequently biasing the shank 4 downwardly in a direction toward the base 70 of the receiver 10 when the assembly 1 is fully assembled. For this to occur, the shank top surface 42 must extend at least slightly into the space of the channel 76 when the retainer structure 12 is snugly seated in the lower part of the receiver cavity 100. The shank 4 and retainer 12 are thereby locked or held in position relative to the receiver 10 by the rod 21 firmly pushing downward on the shank top surface 42.

With reference to FIG. 1, the closure structure or closure top 18 can be any of a variety of different types of closure structures for use in conjunction with the present invention with suitable mating structure on the upstanding arms 72 and 74. In the embodiment shown, the closure top 18 is rotatably received between the spaced arms 72 and 74. The illustrated closure top 18 has a generally cylindrical shaped base 158 with an upwardly extending break-off head 160. The base 158 includes a helically wound guide and advancement structure 161 that is sized, shaped and positioned so as to engage and interlock with the guide and advancement structure 82 on the arms 72 and 74 to provide for rotating advancement of the closure structure 18 into the receiver 10 when rotated clockwise and, in particular, to cover the top or upwardly open portion 77 of the U-shaped channel 76 to capture the rod 21 without splaying of the arms 72 and 74. The guide and advancement structure 161 utilized in accordance with the present invention may take a variety of forms, including the illustrated substantially square thread and also those described in Applicant's U.S. Pat. No. 6,726,689, which is incorporated herein by reference.

The closure structure 18 also operably biases against the rod 21 by advancement and applies pressure to the rod 21 under torquing, so that the rod 21 is urged downwardly against the shank top end surface 42 that extends up into the channel 76. Downward biasing of the shank top surface 42 operably produces a frictional engagement between the rod 21 and surface 42 and also urges the retainer structure 12 toward the base 70 of the receiver 10, so as to frictionally seat the retainer structure external spherical surface 144 fixedly against the partial internal spherical seating surface 102 of the receiver 10, also fixing the shank 4 and retainer structure 12 in a selected, rigid position relative to the receiver 10.

In the embodiment shown, the closure structure break-off head 160 secured to the base 158 at a neck 164 that is sized and shaped so as to break away at a preselected torque that is designed to properly seat the retainer 12 in the receiver 10. The break-off head 160 includes an external faceted surface 165 that is sized and shaped to receive a conventional mating socket type head of a driving tool (not shown) to rotate and torque the closure structure 18. The break-off head 160 may also include a central bore or other drive or manipulation apertures (not shown) for operably receiving manipulating tools.

The closure structure 18 also includes removal tool engagement structure which in the present embodiment is illustrated in phantom as an aperture 168, such as a hex-shaped and axially aligned aperture disposed in the base 158. The aperture 168 is accessible after the break-off head 160 breaks away from the base 158. The aperture 168 is coaxial with the helically wound guide and advancement structure 161 and is designed to receive a driving tool, such as a hex tool of an Allen wrench type, into the aperture 168 for rotating the closure structure base 158 subsequent to installation so as to provide for removal thereof, if necessary. The aperture 168 may take a variety of tool-engaging forms and may include one or more apertures of various shapes, such as a pair of spaced apart apertures, or a left hand threaded bore, or an easy-out engageable step down bore, or a Torx aperture, or a multi-lobular aperture or the like.

With particular reference to FIGS. 5-8, prior to the polyaxial bone screw assembly 1 being placed in use according to the invention, the ring-like retainer 12 is typically first inserted or top-loaded, into the receiver U-shaped channel 76 and then into the cavity 98 through the vertical loading recess 107 to dispose the structure 12 within the inner surface 100 of the receiver 10. Then, the retainer structure 12 is rotated approximately 90 degrees so as to be coaxial with the receiver 10 and then seated in sliding engagement with the seating surface 102 of the receiver 10 as illustrated in FIG. 5. With reference to FIG. 6, the shank capture structure 8 is then inserted or bottom-loaded into the receiver 10 through the bore 104 defined by the neck 103. The retainer structure 12, now disposed in the receiver 10 is coaxially aligned with the shank capture structure 8 so that the lug 36 is received by and moved through the through slot 120 until the bottom surface 114 of the retainer 12 engages the surface 50 of the seat 33. The retainer 12 is then rotated about the axis A of the shank 4 until the lug 36 is received in the cam track 122. With reference to FIGS. 7 and 8, as the retainer 12 is rotated and the lug 36 is moved toward the stop 134, the lug bottom surface 61 frictionally engages the ramped surface 132 of the cam track 122, frictionally locking the retainer 12 between the lug 36 and the seat 33, the retainer 12 now in fixed coaxial relationship with the shank 4. Preferably, the shank 4 and or the retainer 12 are rotated to fully mate such structures at a factory setting that includes tooling for holding and precisely rotating the shank 4 and/or the retainer 12 until locking frictional engagement therebetween is accomplished. With reference to FIG. 7, a holding tool 180 having an inner surface 182 providing a socket for operatively mating with the shank tool engagement structure 40 is used to hold the shank upper portion 8 while in the receiver 10 during mating rotation of the shank upper portion 8 with the retainer 12. Although not shown, it is noted that the retainer structure 12 may also have tooling features, such as a pair of small apertures so that the retainer 12 is also securely held during the rotation of the lug 36 along the cam track 122. Permanent, rigid engagement of the capture structure 8 to the retainer structure 12 may be further supported by the use of adhesive, a spot weld, a deformation, or the like. At this time both the shank 4 and the retainer 12 are in rotatable and swivelable engagement with the receiver 10, while the shank upper-portion 8 and the lower aperture or neck 103 of the receiver 10 cooperate to maintain the shank body 6 in swivelable relation with the receiver 10. Only the retainer 12 is in slidable engagement with the receiver spherical seating surface 102. The shank upper end 41 and the shank body 6 are in spaced relation with the receiver 10. The shank body 6 can be rotated through a substantial angular rotation relative to the receiver 10, both from side to side and from front to rear so as to substantially provide a universal or ball joint.

In use, the assembly 1 is typically screwed into a bone, such as a vertebra (not shown), by rotation of the shank 4 using a driving tool (not shown, but having a socket similar to the socket 182 of the tool 180) that operably drives and rotates the shank 4 by engagement thereof with the tool engagement structure 40 that is in the form of a hexagonally shaped extension head. Preferably, when the driving tool engages the engagement structure 40, an end portion thereof engages the ledge 56 and may also engage a portion of the curved retainer top surface 112, providing additional gripping of the driving tool.

The vertebra (not shown) may be pre-drilled to minimize stressing the bone and have a guide wire (not shown) that is shaped for the cannula 44 inserted to provide a guide for the placement and angle of the shank 4 with respect to the vertebra. A further tap hole may be made using a tap with the guide wire as a guide. Then, the assembly 1 is threaded onto the guide wire utilizing the cannulation bore 44 by first threading the wire into the bottom opening 46 and then out of the top opening 48. The shank 4 is then driven into the vertebra, using the wire as a placement guide.

The rod 21 is eventually positioned within the receiver U-shaped channel 76, and the closure structure or top 18 is then inserted into and advanced between the arms 72 and 74 so as to bias or push against the rod 21. The break-off head 160 of the closure structure 18 is twisted to a preselected torque, for example 90 to 120 inch pounds, to urge the rod 21 downwardly. The shank top end surface 42, because it is rounded to approximately equally extend upward into the channel 76 approximately the same amount no matter what degree of rotation exists between the shank 4 and receiver 10 and because the surface 42 is sized to extend upwardly into the U-shaped channel 76, the surface 42 is engaged by the rod 21 and pushed downwardly toward the base 70 of the receiver 10 when the closure structure 18 biases downwardly toward and onto the rod 21. The downward pressure on the shank 4 in turn urges the retainer structure 12 downward toward the receiver seating surface 102, with the retainer structure surface 144 in frictional engagement with the receiver seating surface 102. As the closure structure 18 presses against the rod 21, the rod 21 presses against the shank. The retainer structure 12 that is now rigidly attached to the shank 4 is in turn urged downwardly and becomes frictionally and rigidly attached to the receiver 10, fixing the shank body 6 in a desired angular configuration with respect to the receiver 10 and rod 21.

If removal of the assembly 1 and associated rod 21 and closure structure 18 is necessary, disassembly is accomplished by using a driving tool of an Allen wrench type (not shown) mating with the aperture 168 and turned counterclockwise to rotate the base 158 and reverse the advancement thereof in the receiver 10. Then, disassembly of the assembly 1 is accomplished in reverse order to the procedure described previously herein for assembly.

With reference to FIGS. 9-17, the reference number 201 generally represents an alternative embodiment of a polyaxial bone screw apparatus or assembly according to the present invention. The assembly 200 includes a shank 204 that further includes a threaded body 206 integral with an upper portion 208; a receiver 210; and an open retainer structure or ring 212. The shank 204, receiver 210 and retainer structure 212 preferably are factory assembled prior to implantation of the shank body 206 into a vertebra (not shown).

With further reference to FIG. 9, also shown is a closure structure 218 for biasing a longitudinal connecting member such as a rod 221 against the shank upper portion 208 which biases the retainer 212 into fixed frictional contact with the receiver 210, so as to fix the rod 221 relative to the vertebra (not shown). The receiver 210 and the shank 204 cooperate in such a manner that the receiver 210 and the shank 204 can be secured at any of a plurality of angles, articulations or rotational alignments relative to one another and within a selected range of angles both from side to side and from front to rear, to enable flexible or articulated engagement of the receiver 210 with the shank 204 until both are locked or fixed relative to each other near the end of an implantation procedure.

The shank 204, best illustrated in FIGS. 9 and 15-17, is elongate, with the shank body 206 having a helically wound bone implantable thread 224 substantially similar to the shank body 6 previously described herein with respect to the assembly 1. The shank 204 has an elongate axis of rotation generally identified by the reference letter E.

A shank neck 226 extends axially upwardly from the shank body 206. Further extending axially upwardly from the neck 226 is the shank upper portion 208 that provides a connective or capture apparatus disposed at a distance from the threaded body 206 and thus at a distance from the vertebra when the body 206 is implanted in the vertebra.

Similar to the assembly 1, the shank upper portion 208 of the assembly 201 is configured for a polyaxial connection between the shank 204 and the receiver 210 and capturing the shank 204 upper portion 108 in the receiver 210. The upper portion 208 generally includes a retainer seat portion 230 that is substantially cylindrical having an upper annular surface 231, an outer cylindrical surface 232 and a lower annular surface 233. The seat portion 230 extends radially outwardly from the neck 226. The upper and lower surfaces 231 and 233 are both disposed substantially perpendicular to the axis E. Located on the neck 226 and near the lower annular seat surface 233 is a laterally extending extension in the form of a lug or tab 236. Extending upwardly axially from the upper annular surface 231 is a tool engagement structure 240 having a top end surface 242. A driving tool (not shown) is configured to fit about the tool engagement structure 240 so as to form a socket and mating projection for both driving and rotating the shank body 206 into the vertebra. Specifically in the embodiment shown in the figures, the tool engagement structure 240 is in the shape of a hexagonally shaped extension head coaxial with both the threaded shank body 206 and the shank upper portion 208. The upper annular surface 231 provides a seating surface for the driving tool (not shown). The top end surface 242 of the shank 204 is preferably curved or dome-shaped as shown in the drawings, for contact engagement or positive mating engagement with the rod 221, when the bone screw assembly 201 is assembled, as shown in FIG. 17 and in any alignment of the shank 204 relative to the receiver 210. In certain embodiments, the surface 242 is smooth. While not required in accordance with practice of the invention, the surface 242 may be scored or knurled to further increase frictional positive mating engagement between the surface 242 and the rod 221.

The shank 204 shown in the drawings is cannulated, having a small central bore 244 extending an entire length of the shank 204 along the axis E. The bore 244 is coaxial with the threaded body 206 and the capture structure outer surface 232. The bore 244 provides a passage through the shank 204 interior for a length of wire (not shown) inserted into the vertebra (not shown) prior to the insertion of the shank body 206, the wire providing a guide for insertion of the shank body 206 into the vertebra (not shown). To provide a biologically active interface with the bone, the threaded shank body 206 may be coated, perforated, made porous or otherwise treated as previously described herein with respect to the shank body 6 of the assembly 1.

With particular reference to FIG. 15, the shank upper portion 208 is sized and shaped to be bottom loaded in the receiver 210 with a compressed retainer 212 connected thereto, the retainer seat portion having an un-compressed or neutral radially extending width sufficient for frictional mating with the retainer 212 as will be described in greater detail subsequently herein. When attached to the shank in an operational position, the retainer 212 engages both the cylindrical surface 232 and the lower annular surface 233 of the shank upper portion 208. It is noted that although a cylindrical surface 232 is shown, the surface may have another shape such as polygonal, spherical, conical or otherwise curved. In the disclosed embodiment, the upper surface 231 is flush with a top surface of the retainer 212 when the seat 230 engages the retainer 212 as will be discussed below. The lug 236 that extends laterally from the neck 226 near the lower annular surface 233 includes a lower or bottom surface 248, a side surface 250 disposed substantially perpendicular to the bottom surface 248 and a curved or sloping surface 252 extending between and connecting the bottom surface 248 and the side surface 248. The side surface 250 is disposed substantially parallel to the axis E. The surfaces 248, 250 and 252 also define an outer curved surface 254 that is cylindrical and coaxial with the neck 226. The surface 252 is preferably sloped or ramped at an angle directed downwardly from the side 250 so as to fully frictionally engage a cam track ramped surface of the retainer 212 as will be described in greater detail below. As with the assembly 1 previously described herein, other surfaces of the lug 236 may be sloped or ramped to result in frictional locking engagement with the cam track of the retainer 212.

Referring to FIGS. 9 and 15-17, the receiver 210 is substantially similar to the receiver 10 of the assembly 1. In particular, for example, the receiver 210 includes a base 270, arms 272 and 274 forming a U-shaped channel 276, a guide and advancement structure 282, a cavity 298 partly defined by a spherical seating surface 302, and a neck 303 defining a bore 304 opening into a base lower exterior 306, that are the same or substantially similar to the respective base 70, arms 72 and 74, U-shaped channel 76, guide and advancement structure 82, cavity 98, spherical seating surface 102, neck 103, bore 104 and lower exterior 106 previously described herein with respect to the bone screw assembly 1.

The retainer structure or ring 212 is used to capture the shank upper portion 208 and retain the upper portion 208 within the receiver 210. The retainer 212, best illustrated in FIGS. 10-14, has an operational central axis that is the same as the rotational axis E associated with the shank 204. The retainer structure 212 has a central bore 310 that passes entirely through the retainer structure 212 from a top surface 312 to a bottom surface 314 thereof. The bottom surface 314 is substantially planar and disposed perpendicular to the axis C. A first inner or upper cylindrical surface 316 defines a portion of the bore 310. A second inner cylindrical surface 317 defines a remainder of the bore 310, the surface 317 having a diameter smaller than a diameter of the surface 316. An annular seat or step 318 connects the first cylindrical surface 316 with the second cylindrical surface 317, the seat 318 being disposed substantially parallel to the top surface 312 and the bottom surface 315 and perpendicular to the cylindrical surfaces 316 and 317. The seat 318 is sized and shaped to fully engage the lower annular surface 233 of the shank upper portion 208. The cylindrical surface 316 is sized and shaped to be slidingly received about the cylindrical surface portion 232 of the shank upper portion 208 while the cylindrical surface 317 is sized and shaped to be slidingly received around the shank neck 226. A cam track or slot 320 is formed in the inner surface 317. The cam track 320 is sized and shaped to receive the lug 236 of the shank upper portion 208 during installation of the retainer 212 on the shank upper portion 208 within the receiver cavity 298. The cam track 320 is sloped or ramped with respect to the axis E and sized and shaped to frictionally engage the lug surfaces 248 and 252, with the retainer 212 seat or step 318 being ultimately frictionally seated on the lower surface 233 of the shank upper portion 208.

As stated above, the retainer 212 is in the form of an open or discontinuous ring, having end surfaces 322 and 323 running through the top surface 312 and the bottom surface 314. The cam track 320 is open at the end surface 322 and sized and shaped to receive the lug 236 therein. The retainer 212 further includes an outer partially spherical surface 326 sized and shaped for slidably mating with the receiver spherical seating surface 302. Formed in the outer surface 326 are at least a pair of expansion grooves 328 running between the top surface 312 and the bottom surface 314, the grooves 328 allowing for the opening or spreading apart of the end surfaces 322 and 323 during installation of the retainer 212 on the shank 204 as will be described in greater detail below. In some embodiments according to the invention, one or more lug 236 surfaces and/or surfaces defining the cam track 320 may include a roughening, ridges or some other treatment to further aid frictional locking of the retainer 212 with respect to the lug 236.

The top surface 312 of the retainer 212 in cooperation with the upper surface or ledge 231 of the shank upper portion 208 provide a surface about the tool engagement structure 240 that is a stable seating surface for the driving tool (not shown). Although not required, it is foreseen that the outer partially spherically shaped surface 326 may be a high friction surface such as a knurled surface or the like.

The elongate rod or longitudinal member 221 that is utilized with the assembly 201 can be any of a variety of implants utilized in reconstructive spinal surgery as described above with respect to the 21 of the assembly 1. The rod 221 normally directly or abuttingly engages the shank top surface 242 and is biased against the dome shank top surface 242, consequently biasing the shank 204 downwardly in a direction toward the base 270 of the receiver 210 when the assembly 201 is fully assembled. For this to occur, the shank top surface 242 must extend at least slightly into the space of the channel 276 when the retainer structure 212 is snugly seated in the lower part of the receiver cavity 302. The shank 204 and retainer 212 are thereby locked or held in position relative to the receiver 210 by the rod 221 firmly pushing downward on the shank top surface 242.

With reference to FIGS. 9 and 17, the closure structure or closure top 218 can be any of a variety of different types of closure structures for use in conjunction with the present invention with suitable mating structure on the upstanding arms 272 and 274. In the embodiment shown, the closure top 218 is rotatably received between the spaced arms 272 and 274. The illustrated closure top 218 is generally cylindrical in shape and includes a helically wound guide and advancement structure 361 that is sized, shaped and positioned so as to engage and interlock with the guide and advancement structure 282 on the arms 272 and 274 to provide for rotating advancement of the closure structure 218 into the receiver 210 when rotated clockwise and, in particular, to cover the top or upwardly open portion of the U-shaped channel 276 to capture the rod 221 without splaying of the arms 272 and 274. The guide and advancement structure 361 utilized in accordance with the present invention may take a variety of forms, including the illustrated substantially square thread and also those described in Applicant's U.S. Pat. No. 6,726,689, which is incorporated herein by reference.

The closure structure 218 also operably biases against the rod 221 by advancement and applies pressure to the rod 221 under torquing, so that the rod 221 is urged downwardly against the shank top end surface 242 that extends up into the channel 276. Downward biasing of the shank top surface 242 operably produces a frictional engagement between the rod 221 and surface 242 and also urges the retainer structure 212 toward the base 270 of the receiver 210, so as to frictionally seat the retainer structure external spherical surface 326 fixedly against the partial internal spherical seating surface 302 of the receiver 210, also fixing the shank 204 and retainer structure 212 in a selected, rigid position relative to the receiver 210.

In the embodiment shown, the closure structure includes a top surface 364 and an opposed bottom substantially planar surface 365. The top surface 364 has an internal drive feature 366 formed thereon shown as a star-shaped or Torx aperture sized and shaped to receive a driving tool (not shown). The aperture 366 may take a variety of tool-engaging forms and may include one or more apertures of various shapes, such as a pair of spaced apart apertures, or a left hand threaded bore, or an easy-out engageable step down bore, hex drive or multi-lobular aperture or the like.

Figure 12:
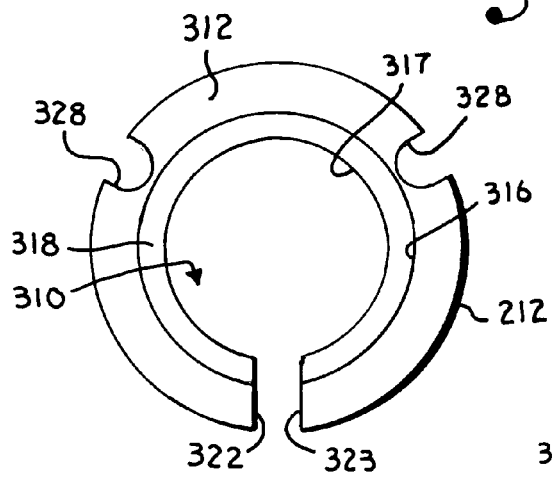
FIG. 12 is an enlarged top plan view of the retainer of FIG. 9.
Figure 14:
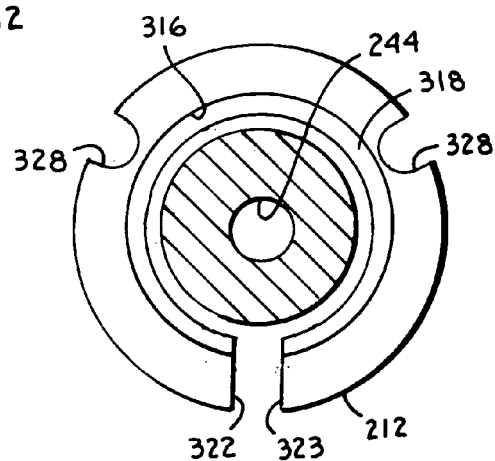
FIG. 14 is an enlarged top plan view similar to FIG. 13 showing the retainer in a subsequent stage of assembly with the shank.
Figure 13:
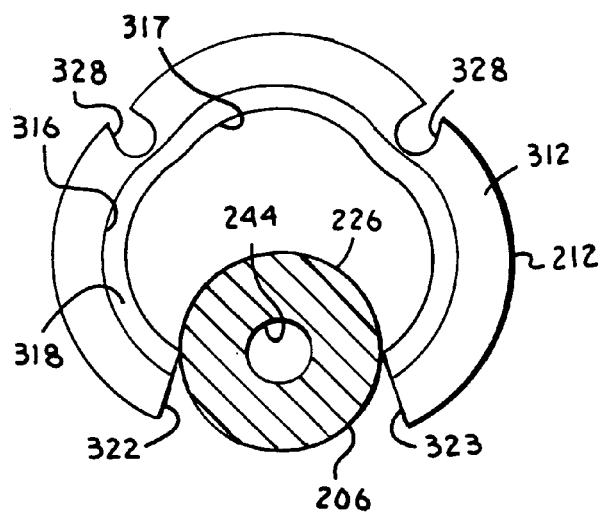
FIG. 13 is an enlarged top plan view similar to FIG. 12, also showing the shank of FIG. 9 with portions broken away to show the detail thereof and showing the retainer in a stage of assembly with the shank.

With particular reference to FIGS. 12-14, prior to the polyaxial bone screw assembly 201 being placed in use according to the invention, the ring-like retainer 212 is first inserted onto the shank 204 at the neck 226. With reference to FIG. 13, the retainer end surfaces 322 and 323 are pulled away from one another, the retainer 212 thereby expanding to receive the shank neck 226 within the inner walls 316 and 317 with the retainer top surface 312 facing the shank upper portion 208. The expansion grooves 328 compress as the retainer 212 is expanded. Once the neck of the shank 204 is past the end surfaces 322 and 323 as shown in FIG. 14, the retainer 212 returns to a neutral non-expanded substantially circular configuration. The retainer 212 is then compressed with the end surfaces 322 and 323 being pushed toward one another to a touching or near touching configuration. While in such a compressed orientation, the shank upper portion 208 and the compressed retainer 212 are up or bottom loaded into the receiver 210 at the neck 303. Once both the upper portion 208 and the retainer 212 are within the receiver cavity 298, pressure is released from the retainer 212 and the end surfaces 322 and 323 are allowed to return to an original spaced and neutral position as illustrated in FIG. 15 with the retainer outer surface 326 in sliding engagement with the receiver seating surface 302. With reference to FIG. 16, the shank capture structure 208 is then lowered into the retainer 212 with the lug 236 disposed between the end surface 322 and the end surface 323. The retainer 212 or the shank 204 is then rotated with respect to the axis E of the shank 104 with the lug 236 entering the cam track 320 at the surface 322. With reference to FIGS. 16 and 17, as the retainer 212 or the shank 208 is rotated, the lug 236 is moved along the sloped cam track 320 until the track terminates or the lug is otherwise fully frictionally engaged with surfaces defining the track 320 and with the retainer annular seating surface 318 fully frictionally engaged with the shank lower annular surface 233, frictionally locking the retainer 212 between the lug 236 and the lower seat or surface 233, the retainer 212 now in fixed coaxial relationship with the shank 204. Preferably, the shank 204 and or the retainer 212 are rotated to fully mate such structures at a factory setting that includes tooling for holding and precisely rotating the shank 204 and/or the retainer 212 until locking frictional engagement therebetween is accomplished. Although not shown, it is noted that the retainer structure 212 may also have tooling features, such as a pair of small apertures so that the retainer 212 is also securely held during the rotation of the lug 236 along the cam track 320. Permanent, rigid engagement of the capture structure 208 to the retainer structure 212 may be further supported by the use of adhesive, a spot weld, a deformation, or the like. At this time both the shank 204 and the retainer 212 are in rotatable and swivelable engagement with the receiver 210, while the shank upper portion 208 and the lower aperture or neck of the receiver 210 cooperate to maintain the shank body 206 in swivelable relation with the receiver 210. Only the retainer 212 is in slidable engagement with the receiver spherical seating surface 302. The shank body 206 can be rotated through a substantial angular rotation relative to the receiver 210, both from side to side and from front to rear so as to substantially provide a universal or ball joint.

In use, the assembly 201 is typically screwed into a bone, such as a vertebra (not shown), by rotation of the shank 204 using a driving tool (not shown) that operably drives and rotates the shank 204 by engagement thereof with the tool engagement structure 240 that is in the form of a hexagonally shaped extension head.

The vertebra (not shown) may be pre-drilled to minimize stressing the bone and have a guide wire (not shown) that is shaped for the cannula 244 inserted to provide a guide for the placement and angle of the shank 204 with respect to the vertebra. A further tap hole may be made using a tap with the guide wire as a guide. Then, the assembly 201 is threaded onto the guide wire utilizing the cannulation bore 244. The shank 204 is then driven into the vertebra, using the wire as a placement guide.

The rod 221 is eventually positioned within the receiver U-shaped channel 276, and the closure structure or top 218 is then inserted into and advanced between the arms 272 and 274 so as to bias or push against the rod 221. The shank top end surface 242, because it is rounded to approximately equally extend upward into the channel 276 approximately the same amount no matter what degree of rotation exists between the shank 204 and receiver 210 and because the surface 242 is sized to extend upwardly into the U-shaped channel 276, the surface 242 is engaged by the rod 221 and pushed downwardly toward the base 270 of the receiver 210 when the closure structure 218 biases downwardly toward and onto the rod 221. The downward pressure on the shank 204 in turn urges the retainer structure 212 downward toward the receiver seating surface 302, with the retainer surface 326 in frictional engagement with the receiver seating surface 302. As the closure structure 218 presses against the rod 221, the rod 221 presses against the shank. The retainer structure 212 that is now rigidly attached to the shank 204 is in turn urged downwardly and becomes frictionally and rigidly attached to the receiver 210, fixing the shank body 206 in a desired angular configuration with respect to the receiver 210 and rod 221.

If removal of the assembly 201 and associated rod 221 and closure structure 218 is necessary, disassembly is accomplished by using a driving tool of Torx wrench type (not shown) mating with the aperture 366 and turned counter-clockwise to rotate the closure structure 218 and reverse the advancement thereof in the receiver 210. Then, disassembly of the assembly 201 is accomplished in reverse order to the procedure described previously herein for assembly.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial bone screw assembly comprising:
   (a) a shank having a body for fixation to a bone and an upper portion, the upper portion having at least one laterally extending lug, the lug being spaced from a top surface of the upper portion;
   (b) a receiver defining an open channel and having a base with a receiver seating surface partially defining a cavity, the open channel communicating with the cavity, the cavity communicating with an exterior of the base through an opening sized and shaped to receive the shank upper portion therethrough; and
   (c) a retainer having an internal surface defining a central bore, the internal surface also defining a sloping cam track, the track receiving the lug and frictionally engaging the lug.
2. The assembly of claim 1 wherein the retainer is a continuous closed ring.
3. The assembly of claim 2 wherein the upper portion has a shank seating surface frictionally engaged with the retainer, the at least one lug located between the shank seating surface and the top surface of the upper portion.
4. The assembly of claim 2 wherein the retainer is loaded into the receiver through the open channel for assembly with the shank upper portion in the cavity.
5. The assembly of claim 1 wherein the retainer is open and discontinuous.
6. The assembly of claim 5 wherein the upper portion has a shank seating surface frictionally engaged with the retainer, the shank seating surface being located between the at least one lug and the top surface of the upper portion.
7. The assembly of claim 5 wherein the retainer is loaded into the receiver in a compressed state through the receiver base opening.
8. The assembly of claim 5 wherein the retainer further includes grooves and is expandable and compressible.
9. In a polyaxial bone screw assembly for surgical implantation and including a shank having an upper end and a threaded body for inserting into a bone and a receiver having an outward opening channel adapted to receive a longitudinal connecting member within the channel, the receiver having a shank receiving opening, the improvement comprising:
   (a) a lug projecting laterally from the shank, the lug spaced from the upper end; and
   (b) a closed retainer having a top, a bottom, an external surface and an internal surface, both the external and internal surfaces running between the top and the bottom surfaces, the internal surface having a slot with at least one cam surface disposed at an angle with respect to the top and bottom surfaces, the external surface being in slidable relation with the receiver, the cam surface frictionally engaging the lug.
10. In a polyaxial bone screw assembly for surgical implantation and including a shank having an upper end and a threaded body for inserting into a bone and a receiver having an outward opening channel adapted to receive a longitudinal connecting member within the channel, the receiver having a shank receiving opening, the improvement comprising:
    (a) a lug projecting laterally from the shank, the lug spaced from the upper end;
    (b) a shank seating surface extending radially from the shank, the shank seating surface being spaced from the upper end and located between the upper end and the lug; and
    (c) an open retainer having a top, a bottom, an external surface and an internal surface, both the external and internal surfaces running between the top and the bottom surfaces, the internal surface having a cam track formed therein, the track running at an angle with respect to the top and bottom surfaces, the external surface being in slidable relation with the receiver, the cam track frictionally engaging the lug and the shank seating surface frictionally engaging the retainer top.
11. A polyaxial bone screw assembly comprising:
    (a) a shank having a body for fixation to a bone and an upper portion with a top surface, the upper portion having a shank structure configured to mate with a retainer;
    (b) a receiver defining an open channel and having a base with a receiver seating surface partially defining a cavity, the open channel communicating with the cavity, the cavity communicating with an exterior of the base through an opening sized and shaped to receive the shank upper portion therethrough; and
    (c) the retainer having an external partial spherical surface for engaging the receiver seating surface and a retainer structure configured to engage the shank structure, the shank and retainer cooperating in such a manner that a partial rotation between the retainer and the shank brings the shank and retainer structures into locking engagement.

12. The assembly of claim 11 wherein the retainer is a continuous closed ring.

13. The assembly of claim 12 wherein:
   (a) the upper portion has a shank seating surface frictionally engaged with the retainer; and
   (b) the shank structure includes at least one lug located between the shank seating surface and the top surface of the upper portion.

14. The assembly of claim 12 wherein the retainer is loaded into the receiver through the open channel for assembly with the shank upper portion in the cavity.

15. The assembly of claim 11 wherein the retainer is open and discontinuous.

16. The assembly of claim 15 wherein:
   (a) the upper portion has a shank seating surface frictionally engaged with the retainer and the shank structure includes at least one lug; and
   (b) the shank seating surface is located between the at least one lug and the top surface of the upper portion.

17. The assembly of claim 15 wherein the retainer is loaded into the receiver in a compressed state through the receiver base opening.

18. The assembly of claim 15 wherein the retainer further includes grooves and is expandable and compressible.

19. The assembly of claim 11 wherein:
   (a) the shank structure includes a lug projecting from the upper portion of the shank; and
   (b) the retainer structure includes a cam surface formed within the retainer and engaged by the lug.

20. The assembly of claim 11 wherein:
   (a) the upper portion includes a shank partial spherical surface engageable with the receiver seating surface when the shank structure is mated with the retainer; and
   (b) the shank spherical surface is located at least partially axial below the retainer spherical surface when the shank structure is mated to the retainer.

21. The assembly of claim 11 wherein the retainer has a spaced apart opposed structure for engaging the shank.

22. A polyaxial bone screw assembly comprising:
   (a) a shank having a body for fixation to a bone and an upper portion, the upper portion that is received in the receiver and that has at least one shank projecting structure for mating with a retainer;
   (b) a receiver defining an open channel and having a base with a receiver seating surface partially defining a cavity, the open channel communicating with the cavity, the cavity communicating with an exterior of the base through an opening sized and shaped to receive the shank upper portion therethrough; and
   (c) the retainer having an external partial spherical surface for engaging the seating surface and a curved ramp structure for receiving and cam engaging the shank projecting structure, wherein a partial rotation between the retainer and the shank brings the structures into locking engagement.

23. A medical implant comprising:
   a) a receiver having a lower portion with a lower opening and an upper portion with a rod receiving channel;
   b) a bone screw shank having an upper portion that is received in the receiver and includes a top surface and a cam surface follower;
   c) a retaining member having a cam surface for a caming engagement with the shank upper portion cam surface follower; and wherein
   d) when the shank is positioned in the receiver, the top surface receives a downward pressure to lock the shank with respect to the receiver.

24. A polyaxial bone screw assembly comprising:
   a) a shank having a body for fixation to a bone and an upper portion, the upper portion having at least one cam following structure for mating with a retainer;
   b) a receiver having an open channel and having a base with a seating surface partially defining a cavity, the open channel communicating with the cavity, the cavity communicating with an exterior of the base through an opening sized and shaped to receive the shank upper portion therethrough; and
   c) the retainer having an external partial spherical surface for engaging the seating surface and a retainer cam track structure for engaging the shank cam follower, wherein a partial rotation between the retainer and shank brings the shank cam follower and retainer cam track structures into locking engagement.

* * * * *